US011283463B2

(12) United States Patent
    Ouzounov et al.

(10) Patent No.: US 11,283,463 B2
(45) Date of Patent: Mar. 22, 2022

(54) SYSTEMS AND METHODS FOR PERFORMING ANALOG-TO-DIGITAL CONVERSION ACROSS MULTIPLE, SPATIALLY SEPARATED STAGES

(71) Applicant: KONINKLIJKE PHILIPS N.V., Eindhoven (NL)

(72) Inventors: Sotir Filipov Ouzounov, Eindhoven (NL); Emil Dimitrov Totev, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/041,593

(22) PCT Filed: Mar. 26, 2019

(86) PCT No.: PCT/EP2019/057600
 § 371 (c)(1),
 (2) Date: Sep. 25, 2020

(87) PCT Pub. No.: WO2019/185633
 PCT Pub. Date: Oct. 3, 2019

(65) Prior Publication Data
 US 2021/0367611 A1    Nov. 25, 2021

(30) Foreign Application Priority Data

Mar. 27, 2018  (EP) .................................... 18164263
 Mar. 27, 2018  (EP) .................................... 18164277

(51) Int. Cl.
    *H03M 1/50*    (2006.01)
    *H03M 3/00*    (2006.01)
    (Continued)

(52) U.S. Cl.
    CPC ................. *H03M 3/30* (2013.01); *A61B 8/00* (2013.01); *A61B 8/5207* (2013.01);
    (Continued)

(58) Field of Classification Search
    CPC .......... H03M 3/30; H03M 1/125; H03M 1/50; H03M 1/164; H03M 3/466; H03M 1/123; A61B 8/5207; A61B 8/00
    See application file for complete search history.

(56) References Cited

U.S. PATENT DOCUMENTS 6,203,498 B1 *  3/2001  Bunce ...................... A61B 8/00
                                                    600/440
7,199,738 B2    4/2007  Han et al.
                (Continued)

FOREIGN PATENT DOCUMENTS

| EP | 1499011 A1 | 1/2005 |
| WO | WO0010638 A2 | 3/2000 |
| WO | 2014195739 A1 | 12/2014 |
| WO | 2017097968 A1 | 6/2017 |

OTHER PUBLICATIONS

Colletta, et al., "A 20-nW 0.25-V Inverter-Based Asynchronous Delta-Sigma Modulator in 130-nm Digital CMOS Process", IEEE Transactions on Very Large Scale Integration (VLSI) Systems, vol. 25, No. 12, Dec. 2017, pp. 3463.
(Continued)

*Primary Examiner* — Joseph J Lauture

(57) ABSTRACT

The invention provides a signal processing system, for transferring analog signals from a probe to a remote processing unit. The system comprises a first ASIC at a probe, which is adapted to receive an analog probe signal. The first ASIC comprises an asynchronous sigma-delta modulator, wherein the asynchronous sigma-delta modulator is adapted to: receive the analog probe signal; and output a binary bit-stream. The system further comprises a second ASIC at
(Continued)

the remote processing unit, adapted to receive the binary bit-stream. The asynchronous may further include a time gain function circuit, the first ASIC may further comprise a multiplexer, the second ASIC may further comprise a time-to-digital converter. The time to digital converter may be a pipelined time-to-digital converter.

15 Claims, 6 Drawing Sheets

(51) Int. Cl.
  *H03M 1/12* (2006.01)
  *A61B 8/08* (2006.01)
  *A61B 8/00* (2006.01)
  *H03M 1/16* (2006.01)
(52) U.S. Cl.
  CPC ............. *H03M 1/125* (2013.01); *H03M 1/50* (2013.01); *H03M 1/123* (2013.01); *H03M 1/164* (2013.01); *H03M 3/466* (2013.01)

(56) References Cited

U.S. PATENT DOCUMENTS

| | | |
|---|---|---|
| 2007/0236374 A1 | 10/2007 | Brueske et al. |
| 2013/0289426 A1 | 10/2013 | Lakshminarayan et al. |
| 2016/0126968 A1 | 5/2016 | Lesso et al. |
| 2016/0344402 A1 | 11/2016 | Koscielnik et al. |

OTHER PUBLICATIONS

Daniels, et al., "A/D Conversion Using Asynchronous Delta-Stigma Modulation and Time-to-Digital Conversion", IEEE Transactions on Circuits and Systems, I: Regular Papers, vol. 57, No. 9, Sep. 2010, pp. 2404-2412.

Bickle, et al., "Time gain compensation" Radiology Reference Article, Radiopaedia.org, Dec. 25, 2017, Retrieved from the Internet: URL:https://web.archive.org/web/20171225171703/https://radiopaedia.org/articles/time-gain-compensation, 7 pages (Abstract).

International Search and Written Opinion for International Application No. PCT/EP2019/057600, filed Mar. 26, 2019, 24 pages.

Ouzounov, et al., "Analysis and Design of High-Performance Asynchronous Sigma-Delta Modulators With a Binary Quantizer", IEEE Journal of Solid-State Circuits, vol. 41, No. 3, Mar. 2006, pp. 588-596.

Zhou, et al., "Asynchronous Compressed Beamformer for Portable Diagnostic Ultrasound Systems", IEEE Transactions on Ultrasonics, Ferroelectrics, and Frequency Control, vol. 61, No. 11, Nov. 2014, pp. 1791-1801.

G. Engindeniz, "Design, analysis and evaluation of sigma-delta based beamformers for medical ultrasound imaging applications", A Thesis submitted in Partial Fulfilment of the Requirements of the University of Westminster for the Degreee of Doctor of Philisophy, University of Forward Thinking Westminster, 227 pages.

Lie, et al., "Ultrasonic Beamforming with Delta-sigma Modulators", Proceedings of the 10th WSEAS International Conference on Circuits, Vouliagmeni, Athens, Greece, Jul. 10-12, 2002, pp. 344-349.

\* cited by examiner

SYSTEMS AND METHODS FOR PERFORMING ANALOG-TO-DIGITAL CONVERSION ACROSS MULTIPLE, SPATIALLY SEPARATED STAGES

RELATED APPLICATIONS

This application is the U.S. National Phase application under 35 U.S.C. § 371 of International Application No. PCT/EP2019/057600, filed on Mar. 26, 2019, which claims the benefit of both European Application No. 18164263.8, filed Mar. 27, 2018, and European Application No. 18164277.8, filed Mar. 27, 2018. These applications are hereby incorporated by reference herein.

FIELD OF THE INVENTION

This invention relates to the field of signal processing, and more specifically to the field of signal processing across multiple, spatially separated stages within an ultrasound system.

BACKGROUND OF THE INVENTION

In the construction of an ultrasound probe, high voltage technologies are required to drive the acoustic transducer elements and amplify the received signals. However, these high voltage technologies are not suitable for the implementation of more complex functions, such as analog-to-digital conversion (ADC) and digital signal processing (DSP), simply due to the large feature size of the transistors in these technology nodes, which leads to prohibitively high area, and power, consumption and low speed. This issue drives system choices toward the high voltage integrated circuit containing a minimal functionality that is sufficient to transport the signal to a separate low voltage integrated circuit capable of performing the required signal processing in order to generate an ultrasound image. A low voltage integrated circuit implies small feature size transistors that can have state-of-art capabilities in terms of speed and power consumption, whilst maintaining their small size.

Typically, the high voltage integrated circuit is located within the ultrasonic probe itself, whereas, the low voltage integrated circuit is located within a back end processing unit connected to the probe via a cable. Thus, the analog signals received by the high voltage integrated circuit must be propagated between the high and low voltage integrated circuits. Analog signal propagation is inherently difficult as the signal integrity must be maintained in order to properly interpret it at the receiving end. This is further complicated by the variable propagation distance along the cable, signal dissipation within the interconnecting cable lines and the presence of multiple interfering signals. In addition, new and emerging applications typically require an increasing number of ultrasound transducers in a 2D configuration, which in turn leads to an increase in the amount of acquired data channels that have to be propagated to the back end processing system.

Further, the limitations of analog beamforming, which is typically used at the front-end to reduce the amount of data that is transported in an analog way to the backend, must be considered. Analog beamforming introduces limitations on the achievable performance in terms of maximum dynamic range, spatial resolution and maximum frame-rate.

Finally all the data has to be transported in a robust way to the beam-former. For many non-multiplexed channels, this can be a difficult and costly process due to the many parallel cables required. Due to the high number of channels in an acoustic probe, it is beneficial to multiplex as many channels as possible on a single line; however, there are many difficulties associated with the multiplexing of multiple analogue signals.

There is therefore a need to provide a robust means of propagating the analog signals from one integrated circuit to another without requiring significant additional hardware.

SUMMARY OF THE INVENTION

The invention is defined by the claims.

According to examples in accordance with an aspect of the invention, there is provided a signal processing system, for transferring analog signals from a probe to a remote processing unit, comprising:
  a first ASIC at the probe, adapted to receive an analog probe signal, wherein the first ASIC comprises:
    an asynchronous sigma-delta modulator, wherein the asynchronous sigma-delta modulator is adapted to:
      receive the analog probe signal; and
      output a binary bit-stream;
  a second ASIC at the remote processing unit, adapted to receive the binary bit-stream.

The probe, for example an ultrasound probe, is adapted to receive an analog signal. The probe forms part of a signal processing system, the other part of which is the remote processing unit, which is typically separated from the probe by some variable distance. In some applications, the remote processing unit may be located within the same housing as the probe and may even occupy the same printed circuit board (PCB); whereas, in other applications, the remote processing unit may be separated from the probe by several meters of cable.

Maintaining the integrity of the analog signal is central to reliably interpreting the signals received by the probe using the remote processing unit. Accurate interpretation is particularly important for medical applications such as ultrasound. It is typically difficult to maintain signal integrity when propagating analog signals, particularly where those analog signals are weak, or where multiple analog signals are being propagated in parallel and are subject to interference. Further, it is costly to propagate analog signals over a substantial distance as this requires impedance matching, which in turn will be dependent on the type and length of the cable.

By performing asynchronous sigma-delta modulation on the analog signals, an analog signal is transformed into a digital time-domain signal, in which amplitude information is encoded in the time domain, thereby allowing the signal to be propagated to the remote processing unit with greater robustness and with less susceptibility to interference. In addition, it is possible to implement a massively parallel read-out of all individual transducers in a robust manner; whereas, the alternative of performing analog read-out and digitization in the first ASIC is far more difficult to realize.

According to examples in accordance with an aspect of the invention, there is provided a signal processing system (100), for transferring analog signals from a probe to a remote processing unit, comprising:
  a first ASIC at the probe, adapted to receive an analog probe signal acquired from an imaging depth within a subject, wherein the first ASIC comprises:
    an asynchronous sigma-delta modulator, wherein the asynchronous sigma-delta modulator is adapted to:
      receive the analog probe signal; and
      output a binary bit-stream;

a second ASIC at the remote processing unit, adapted to receive the binary bit-stream, and wherein:

the asynchronous sigma-delta modulator comprises:
a time gain function circuit adapted to alter a time gain function of the asynchronous sigma-delta modulator based on the imaging depth, wherein the time gain function is adapted to:
control a feedback gain of the asynchronous sigma-delta modulator, thereby controlling a dynamic range of the asynchronous sigma-delta modulator.

Asynchronous sigma-delta modulators are typically capable of being programed to accommodate a large dynamic range of incoming signals. However, due to the nature of ultrasound signals, where longer signal acquisition windows lead to smaller signal amplitudes, it is often not possible to cover all of the incoming signal amplitudes with a fixed dynamic range.

By providing a time gain function circuit, having an adjustable time gain function, within a feedback loop of the asynchronous sigma-delta modulator, it is possible to control the dynamic range of the asynchronous sigma-delta modulator such that the instantaneous (at each control setting) dynamic range is adjusted for the amplitude of the expected incoming signal. Thus, the dynamic range of the asynchronous sigma-delta modulator may be adjusted over time by way of the time gain function circuit. Typically, the adjustment is performed over time due to the relationship with time and a given scan depth. However, the adjustment may also be done by the user, for example in a non-time synchronized way in order to optimize the current dynamic range to a desired viewing property such as lowering the detectable signal levels for imaging smaller depths.

In an embodiment, the signal processing system further comprises a data channel adapted to propagate the binary bit-stream from the first ASIC to the second ASIC.

The data channel may propagate the binary bit-stream across variable distances depending on the application. For example, in a typical ultrasound system, the remote processing unit may be located on the same PCB as the probe, meaning that the data channel would cover only a short distance. Alternatively, in the case of an ultrasound catheter, the data channel may be adapted to propagate the binary bit-stream across several meters in order to reach the remote processing unit.

In some embodiments, the first ASIC operates at a voltage greater than or equal to 1.8V, for example 2.5V, and wherein the second ASIC operates a voltage less than or equal to 1.8V, for example 1.1V.

In this way, it is possible to house components with a higher voltage requirement on the first ASIC and those with a lower voltage requirement on the second, thereby eliminating the need to sacrifice the efficiency of the various components by operating them all at the same voltage. In addition, this division between the first and second ASICs provides the capability for driving and biasing the ultrasound transducers with the high voltages, for example 75V, required for their operation.

In an arrangement, the asynchronous sigma-delta modulator comprises a low noise amplifier.

In this way it is possible to amplify low amplitude signals, such as deep ultrasound reflection signals acquired towards the end of the acquisition window, without significantly degrading the signal-to-noise ratio. By integrating the low noise amplifier into the asynchronous sigma-delta modulator it is possible to reduce the complexity and implementation cost of the signal processing system.

In a further arrangement, the asynchronous sigma-delta modulator further comprises a feedback capacitor connected with:
an output of the low noise amplifier; and
an input of the low noise amplifier.

Thus, the LNA may be configured as a charge, or current, integrator by way of the feedback capacitor. The feedback signal may be added at the LNA input in either current or charge form depending on the virtual ground provided by the LNA at that input node.

In an embodiment, the asynchronous sigma-delta modulator further comprises a low-pass filter.

In various embodiments, the asynchronous sigma-delta modulator further comprises an asynchronous binary quantizer.

In an arrangement, the asynchronous sigma-delta modulator comprises a feedback digital-to-analog converter.

In this way, through the characteristics of the low-pass filter and the hysteresis of the asynchronous quantizer, it is possible to control the phase shift of the signals within the asynchronous sigma-delta modulator loop such that the self-oscillations reach a frequency of greater than or equal to 10 times the Nyquist frequency of the input signal band, thereby reducing the number of spurious signals entering the signal band due to high amplitude input signals.

In some arrangements, the first ASIC further comprises an acoustic transducer element, wherein the acoustic transducer element is adapted to receive an incoming acoustic signal and output the acoustic signal. Alternatively, the acoustic transducer is a separate transducer element, such as a piezoelectric transducer, that is electrically connected to the first ASIC.

In an embodiment, the second ASIC comprises a demodulator.

In this way, the second ASIC may extract information, such as an amplitude of the acoustic signal received by the first ASIC, based on the binary bit-stream generated by the asynchronous sigma-delta modulator.

In a further embodiment, the demodulator is adapted to:
receive the binary bit stream; and
output a reconstructed analog signal; and
the second ASIC further comprises an analog-to-digital converter adapted to receive the reconstructed analog signal.

In various embodiments:
the probe is an ultrasonic probe; and
the remote processing unit is a back-end signal processing unit.

In this way, it is possible to reliably transfer the acoustic ultrasound signals received by the probe to the remote processing unit by transforming the signals into a binary bit-stream. This transfer may occur over various distances depending on the application. For example, in a conventional ultrasound system the probe and remote processing unit may be located within the same probe housing; whereas, in an ultrasound catheter the probe and remote processing unit may be separated by several meters of cable.

According to examples in accordance with an aspect of the invention, there is provided a method for transferring analog signals from a probe to a remote processing unit, the method comprising:
receiving an analog signal at a first ASIC at the probe;
performing asynchronous sigma-delta modulation on the analog signal, thereby generating a binary bit-stream; and
receiving the binary bit-stream from the data channel at the second ASIC at the remote processing unit.

According to examples in accordance with an aspect of the invention, there is provided a method for transferring analog signals from a probe to a remote processing unit, the method comprising:

receiving an analog signal from an imaging depth within a subject at a first ASIC at the probe;

performing asynchronous sigma-delta modulation on the analog signal, by way of an asynchronous sigma-delta modulator, thereby generating a binary bit-stream; and receiving the binary bit-stream from the data channel at the second ASIC at the remote processing unit, and wherein:

performing asynchronous sigma-delta modulation on the analog signal comprises:

altering a time gain function of the asynchronous sigma-delta modulator based on the imaging depth, wherein the time gain function is adapted to:

control a feedback gain of the asynchronous sigma-delta modulator, thereby controlling a dynamic range of the asynchronous sigma-delta modulator.

In an embodiment, the analog signal comprises an ultrasound signal.

According to examples in accordance with an aspect of the invention, there is provided a computer program comprising computer program code means which is adapted, when said computer program is run on a computer, to implement the method described above.

According to examples in accordance with an aspect of the invention, there is provided an asynchronous sigma-delta modulator, wherein the asynchronous sigma-delta modulator comprises:

a time gain function circuit adapted to alter a time gain function of the asynchronous sigma-delta modulator, wherein the time gain function is adapted to:

control a feedback gain of the asynchronous sigma-delta modulator, thereby controlling a dynamic range of the asynchronous sigma-delta modulator.

In an embodiment, the time gain function circuit comprises a digital-to-analog converter having a switched current array, the switched current array comprising:

a plurality of current sources, wherein each current source provides a different current;

a plurality of switches, wherein each switch is connected to a current source and wherein:

when the switch is in a closed position, the associated current source is activated; and when the switch is in an open position, the associated current source is deactivated; and a control interface, adapted to control the position of the plurality of switches.

The feedback signal of an ASDM is typically implemented as a current controlled by the binary states of the output or by a source of electrical charge (e.g. a capacitor), discharged by the integration capacitor in the LNA feedback, while the discharge process is again controlled by the output binary state.

In this way, the time gain function may be controlled by the number of switches in each position. By implementing the current sources such that each current is different, it is possible to achieve a wide variety of dynamic ranges of the asynchronous sigma-delta modulator through the time gain function.

In a further embodiment, the control interface comprises a user interface adapted to receive a user input.

In a yet further embodiment, the user input comprises a designation for the positions of each of the plurality of switches.

In another, or further, embodiment, the user input comprises a desired dynamic range of the asynchronous sigma-delta modulator.

In this way, a user may be able to manually alter the dynamic range of the asynchronous sigma-delta modulator. This may occur directly, for example selecting which switches of the switched current array should be open or closed, or it may occur through an indirect selection of a user, for example selecting a desired function that in turn leads to the altering of the switch positions of the switched current array.

In an arrangement, the plurality of current sources each comprises a switched capacitor.

According to examples in accordance with an aspect of the invention, there is provided a system for controlling the dynamic range of an asynchronous sigma-delta modulator, the system comprising:

an asynchronous sigma-delta modulator as claimed in any preceding claim; and an amplitude detector adapted to provide a control signal to the asynchronous sigma-delta modulator, wherein the control signal is adapted to alter the time gain function of the time gain function circuit.

In an embodiment, the asynchronous sigma-delta modulator comprises a controller adapted to automatically alter the time gain function of the time gain function circuit based on the control signal.

In this way, it is possible to fully automate the altering of the time gain function, and so the dynamic range, of the asynchronous sigma-delta modulator.

In an arrangement, the amplitude detector comprises a counter.

In an embodiment, the amplitude detector is adapted to receive an output of the asynchronous sigma-delta modulator.

In a further embodiment, the control signal is based on an amplitude of the output of the asynchronous sigma-delta modulator.

By detecting the amplitude of the output of the asynchronous sigma-delta modulator directly, it is possible to more accurately automate the adjusting of the dynamic range of the asynchronous sigma-delta modulator in response the incoming signals, thereby increasing the accuracy of the output signal. In addition, the asynchronous sigma-delta modulator feedback loop may also prevent overload from large input signals, or may be used in combination with gain boosting in order to enable the reception of small signals from a greater depth.

Alternatively, the amplitude detection may be performed on the signal before passing to the quantizer in the asynchronous sigma-delta modulator loop as the signal amplitude at this point will be proportional to the amplitude of the input signal.

In some embodiments, the system further comprises a low-pass filter connected in series with the asynchronous sigma-delta modulator and the amplitude detector.

In various arrangements, the system further comprises an ultrasonic transducer.

According to examples in accordance with an aspect of the invention, there is provided a method for controlling the dynamic range of an asynchronous sigma-delta modulator, the method comprising:

obtaining an analog signal;

performing asynchronous sigma-delta modulation on the analog signal, thereby generating a binary bit-stream;

altering a time gain function of a time gain function circuit within the asynchronous sigma-delta modulator based on a signal of the asynchronous sigma-delta modulator;

controlling a feedback gain of the asynchronous sigma-delta modulator based on the time gain function, thereby controlling the dynamic range of the asynchronous sigma-delta modulator.

In an embodiment, the controlling of the time gain function of the time gain function circuit comprises:

performing amplitude detection on the binary bit-stream, thereby generating output amplitude data;

generating a control signal based on the output amplitude data; and altering the time gain function of the time gain function circuit based on the control signal.

According to examples in accordance with an aspect of the invention, there is provided a system for performing analog-to-digital conversion, the system comprising:

a probe having a first ASIC, wherein the first ASIC is adapted to:
  receive an analog signal; and
  output a binary bit-stream comprising asynchronous time-domain pulses;
a processing unit having a second ASIC, wherein the second ASIC comprises a time-to-digital converter adapted to:
  receive the binary bit-stream; and
  generate a digital output from the binary bit-stream based on time-to-digital conversion; and
a data channel adapted to propagate the binary bit-stream from the first ASIC to the second ASIC, wherein the first and second ASICs are spatially separated.

The probe, for example an ultrasound probe, is adapted to receive an analog signal. The probe forms part of a signal processing system, the other part of which is the processing unit, which is typically separated from the probe by some variable distance. In some applications, the remote processing unit may be located within the same housing as the probe and may even occupy the same PCB; whereas, in other applications, the remote processing unit may be separated from the probe by several meters of cable.

Maintaining the integrity of the analog signal is central to reliably interpreting the signals received by the probe using the processing unit. This is particularly important in cases of medical applications such as ultrasound. It is typically difficult to maintain signal integrity when propagating analog signals, particularly where those analog signals are weak, or where multiple analog signals are being propagated in parallel and are subject to interference. Further, it is costly to propagate analog signals over a substantial distance as this requires impedance matching, which in turn will be dependent on the type and length of the cable.

By processing the analog signals in order to generate digital time-domain signals, in which amplitude information may be encoded, it is possible for the signal to be propagated to the remote processing unit with greater robustness and with less susceptibility to interference. The digital time-domain signals may then be interpreted by the remote processing unit, using time-to-digital conversion, in order to generate digital data for interpreting the original analog signals, without the difficulty of analog signal propagation. By employing time-to-digital conversion at the remote processing unit to perform the decoding, it is possible to directly digitize the time-domain signals.

In an embodiment, the time-to-digital converter comprises a pipeline time-to-digital converter, the pipeline time-to-digital converter comprising:

a coarse time-to-digital converter, wherein the coarse time-to-digital converter is adapted to:
  receive the binary bit-stream; and
  output:
    a coarse digital output; and
    a coarse residue time; and
a fine time-to-digital converter block, adapted to receive the coarse residue time, wherein the fine time-to-digital converter block comprises:
  one or more fine time-to-digital converters connected in series, each adapted to:
    receive an incoming residue time from the previous fine, or coarse, time-to-digital converter in the series;
    output an outgoing residue time to the subsequent fine time-to-digital converter in the series; and
    output a fine digital output.

In an embodiment, the first ASIC comprises an asynchronous sigma-delta modulator.

In this way, it is possible to convert the analog signals into the binary bit stream without the need for a clock signal, thereby reducing the number of components required to transform the analog signals into digital time-domain signals.

In some embodiments, the asynchronous sigma-delta modulator comprises a low noise amplifier.

In this way it is possible to amplify low amplitude signals, such as deep ultrasound reflection signals acquired towards the end of the acquisition window, without significantly degrading the signal-to-noise ratio.

In an arrangement, the asynchronous sigma-delta modulator comprises a low-pass filter.

In various arrangements, the asynchronous sigma-delta modulator comprises an asynchronous quantizer.

In an embodiment, the asynchronous sigma-delta modulator comprises a digital-to-analog converter.

In this way, it is possible to control the phase shift of the signals within the asynchronous sigma-delta modulator loop such that the self-oscillations reach a frequency of greater than or equal to 10 times the Nyquist frequency of the input signal band, thereby reducing the number of spurious signals entering the signal band due to high amplitude input signals.

In an embodiment, the first ASIC operates at a voltage greater than or equal to 1.8V, for example 2.5V.

In an arrangement, the second ASIC operates a voltage less than or equal to 1.8V, for example 1.1V.

In this way, it is possible to house components with a higher voltage requirement on the first ASIC and those with a lower voltage requirement on the second, thereby eliminating the need to sacrifice the efficiency of the various components by operating them all at the same voltage.

In an embodiment, the data channel comprises a single line propagation channel.

According to examples in accordance with an aspect of the invention, there is provided a method for performing analog-to-digital conversion on analog signals across a probe and a remote processing unit, the method comprising:

obtaining an analog signal at a first ASIC at the probe;

processing the analog signal using the first ASIC, thereby generating a binary bit-stream based on the analog signal, wherein the binary bit-stream comprises asynchronous time-domain pulses;

propagating the binary bit-stream from the first ASIC to a second ASIC at the processing unit, wherein the second ASIC is spatially separated from the first;

performing time-to-digital conversion on the binary bit-stream by way of a time-to-digital converter housed on using the second ASIC, thereby generating a digital output.

In an embodiment, the processing of the analog signal using a first ASIC comprises performing asynchronous sigma-delta modulation on the analog signal.

In some embodiments, the propagating of the binary bit-stream from the first ASIC to the second ASIC comprises performing single line propagation.

In an arrangement, the analog signal comprises an ultrasound signal.

According to examples in accordance with an aspect of the invention, there is provided a computer program comprising computer program code means which is adapted, when said computer program is run on a computer, to implement the method described above.

According to examples in accordance with an aspect of the invention, there is provided a method for multiplexing a plurality of analog signals each from a separate channel, the method comprising:

obtaining the plurality of analog signals each analog signal being obtained from a separate channel, wherein each separate channel is associated with a channel identifier;

performing asynchronous sigma-delta modulation on each of the plurality of analog signals, thereby generating a plurality of quantized time domain signals based on the plurality of analog signals, wherein each quantized time domain signal comprises one or more edge timing events, an edge timing event relating to a signal edge within the quantized time domain signal; and multiplexing, in an asynchronous manner, the plurality of quantized time domain signals based on the one or more edge timing events of each signal and the channel identifier, thereby generating a multiplexed signal in which edge timing events are associated with channel identifiers.

The propagation of many signals in parallel can be difficult and costly; however, the multiplexing of multiple analog signals is extremely difficult to achieve.

Thus, by processing the analog signals in order to generate digital time-domain signals, it is possible to multiplex the multiple signals with greater ease. Performing this processing in an asynchronous manner allows for the multiplexing to be performed without the need for a clock. In addition, the inclusion of channel identifiers with the edge timing events allows the multiplexed signal to be separated according to channel after propagation, allowing the multiplexed signal to be interpreted by a back end processing system.

By performing asynchronous sigma-delta modulation, each of the plurality of analog signals is transformed into a binary bit-stream in the time domain. By performing the sigma-delta modulation in an asynchronous manner, the need for a clock signal is removed, thereby reducing the number of components required to perform the multiplexing operation and the power dissipation of the circuit itself.

In an embodiment, the multiplexing of the plurality of quantized time domain signals comprises:

for each quantized time domain signal:
identifying an edge timing event; and
labelling the edge timing event with a channel identifier based on the channel from which the associated analog signal was obtained; and
generating a multiplexed signal based on the plurality of quantized time domain signal, wherein the multiplexed signal includes the labelled edge timing events.

By labelling each edge timing event with a channel identifier, it is possible to extract the information from the multiplexed signal on a per channel basis. In this way, the multiplexed signal may carry both timing and channel signal data.

In some embodiments, the edge timing event comprises a rising signal edge.

In an arrangement, the edge timing event comprises a falling signal edge.

By identifying the rising and falling edges of the signals as an edge timing event, it is possible to convey a greater depth of information within the multiplexed signal, thereby allowing the multiplexed signal to be decoded at a later stage.

In an embodiment, the method further comprises decoding the multiplexed signal.

In a further embodiment, decoding the multiplexed signal comprises performing time-to-digital conversion on the multiplexed signal.

The decoding of the multiplexed signal allows for the multiplexed signal to be interpreted, for example, after being propagated to a separate processing location. In this way, it is possible to combine information from a plurality of different signal sources into a single signal, transmit said signal in a simple and robust manner and interpret it at a separate location.

In another embodiment, the decoding comprises time-stamping each edge timing event of the multiplexed signal.

In yet another embodiment, the decoding comprises recording a time between receiving each edge timing event of the multiplexed signal.

By timestamping, and/or measuring the time between receiving, each edge timing event it is possible to determine the relative timings of each event. In this way, and taking into account the channel identifiers of each of the edge timing events, it is possible to more accurately interpret the original analog signals from the multiplexed signal.

In an arrangement, the decoding comprises reconstructing the plurality of analog signals in the digital domain.

According to examples in accordance with an aspect of the invention, there is provided a computer program comprising computer program code means which is adapted, when said computer program is run on a computer, to implement the method described above.

According to examples in accordance with an aspect of the invention, there is provided a system for multiplexing a plurality of analog signals, the system comprising:

an analog signal receiver comprising a plurality of channel each adapted to obtain an analog signal, and wherein each channel is associated with a channel identifier;

a signal processor comprising an asynchronous sigma-delta modulator and adapted to perform asynchronous sigma-delta modulation on each of the plurality of analog signals, thereby generating a plurality of quantized time domain signals based on the plurality of analog signals, wherein each quantized time domain signal comprises one or more edge timing events, an edge timing event relating to a signal edge within the quantized time domain signal; and a multiplexer adapted to multiplex, in an asynchronous manner, the plurality of time domain signals based on the one or more edge timing events of each signal and the channel identifier, thereby generating a multiplexed signal in which edge timing events are associated with channel identifiers.

In an embodiment, the analog signal receiver comprises an ultrasonic transducer.

In an arrangement, the system further comprises a time-to-digital converter.

According to examples in accordance with an aspect of the invention, there is provided a pipeline time-to-digital converter, the pipeline time-to-digital converter comprising:

a coarse time-to-digital converter, wherein the coarse time-to-digital converter is adapted to:
receive an incoming signal; and
output:
a coarse digital output; and
a coarse residue time; and
a fine time-to-digital converter block, adapted to receive the coarse residue time, wherein the fine time-to-digital converter block comprises:
one or more fine time-to-digital converters connected in series, each adapted to:
receive an incoming residue time from the previous fine, or coarse, time-to-digital converter in the series;
output an outgoing residue time to the subsequent fine time-to-digital converter in the series; and
output a fine digital output.

Typically, in time-to-digital converter designs, there exists a trade-off between resolution and dead time (the time between the end of a measurement and the commencement of a new one). It is possible to maximize both parameters; however, this comes at the cost of excessive power consumption, which, in systems such as an ultrasound system, is not feasible.

The coarse time-to-digital converter operates at a low frequency in order to maintain a low power consumption. The error in the measurement performed by the coarse time-to-digital converter then needs to be determined in order to achieve a high resolution. This error, referred to as time residue, is measured by the subsequent fine time-to-digital converter, which in turn produces an error that is measured by a further fine time-to-digital converter, and so on until the desired resolution is reached.

In addition, while the block of fine time-to-digital converters are processing the residue time of the initial coarse time-to-digital converter, the latter may begin another time measurement, thereby reducing the dead-time of the whole system.

In an embodiment, the coarse time-to-digital converter comprises a ring oscillator.

In a further embodiment, the ring oscillator comprises a plurality of inverters.

In another, or further, embodiment the ring oscillator comprises a plurality of delay cells.

By employing a ring oscillator within the coarse time-to-digital converter, it is possible for the time-to-digital converter to generate its own clock signal, thereby eliminating the need to include a separate external clock for the system. In this way, the complexity and power demand of the coarse time-to-digital converter may be reduced.

The inclusion of delay cells within the ring oscillator may result in a higher resolution of the signal, with a potential time resolution of less than 1 ps, and a reduction in noise.

In an arrangement, the coarse time-to-digital converter comprises a time amplifier.

In a further arrangement, the time amplifier is adapted to generate a pulse train.

In a yet further embodiment, the pulse train amplifier is a D flip-flop pulse train time amplifier.

A time-to-digital converter operates at a given time resolution, accepting an input signal once per given time interval according to its operating resolution. If an input signal, for example a pulse, were to arrive at the input having a width lower than the operating resolution of the time-to-digital converter, the time-to-digital converter would be incapable of measuring the signal.

By including a time amplifier within the time-to-digital converter, it is possible to artificially widen the pulse width of an incoming signal by a given factor, thereby making it possible for the signal to be measured by the time-to-digital converter without requiring a significant increase in the hardware of the time-to-digital converter that would otherwise be required to significantly improve the resolution.

A pulse train amplifier allows for an accurate, linear gain that is simple to program to reach a desired extension in the input time range. It is possible to implement the pulse train amplifier using a D flip-flop architecture.

It is possible to reduce the offset introduced to the pulse train generated by the pulse train amplifier, by implementing irregularly distributed delays between successive elements of the (gated) delay line, which forms part of the pulse train amplifier. The allocation ratio of the delays is technology dependent and may be vary across implementations.

In an embodiment, the coarse time-to-digital converter comprises a selector unit.

In a further embodiment, the selector unit comprises a D flip-flop.

In another, or further, embodiment, the selector unit comprises a 1-hot converter.

In yet another, or further, embodiment, the selector unit comprises a binary encoder.

In this way, the selector unit may be implemented in a relatively simple manner and may yield an encoded word representing the delay straight away.

In an arrangement, the series of one or more fine time-to-digital converter each comprises:
a 1.5-bit time-to-digital converter; and
a time amplifier.

The 1.5-bit time-to-digital converter allows for a simple implementation of the fine time-to-digital converter block. The type of time-to-digital converter used to implement the fine time-to-digital converters may vary depending upon the implementation of the pipelined time-to-digital converter.

According to examples in accordance with an aspect of the invention, there is provided a method for performing time-to-digital conversion, the method comprising:
obtaining an incoming signal;
performing a coarse time-to-digital conversion on the incoming signal, thereby generating:
a coarse digital output; and
a coarse residue time; and
performing a series of one or more fine time-to-digital conversions on an incoming residue time, thereby generating:
an outgoing residue time; and
a fine digital output;
wherein the incoming residue time comprises:
the coarse residue time generated by the coarse time-to-digital converter; or
the outgoing residue time generated by a previous fine pipeline time-to-digital converter in the series of one or more fine time-to-digital converters.

In an embodiment, the incoming signal comprises a series of time domain pulses.

According to examples in accordance with an aspect of the invention, there is provided a computer program comprising computer program code means which is adapted, when said computer program is run on a computer, to implement the method described above.

BRIEF DESCRIPTION OF THE DRAWINGS

Examples of the invention will now be described in detail with reference to the accompanying drawings, in which.

DETAILED DESCRIPTION OF THE EMBODIMENTS

In a first aspect, there is provided a signal processing system, for transferring analog signals from a probe to a remote processing unit. The system comprises a first ASIC at a probe, which is adapted to receive an analog probe signal. The first ASIC comprises an asynchronous sigma-delta modulator, wherein the asynchronous sigma-delta modulator is adapted to: receive the analog probe signal; and output a binary bit-stream. The system further comprises a second ASIC at the remote processing unit, adapted to receive the binary bit-stream.

Figure 1:
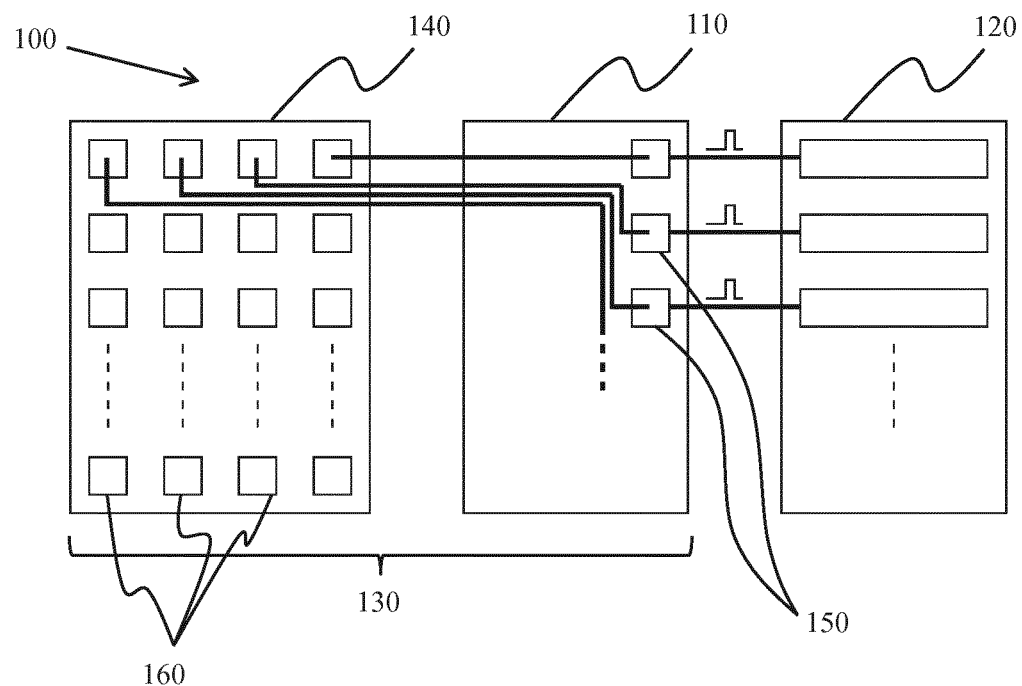
FIG. 1 shows a schematic of a signal processing system.

FIG. 1 shows a schematic of the signal processing system 100. The signal processing system comprises a first ASIC 110 and a second ASIC 120, with the first ASIC located on a probe 130 and the second ASIC located on a remote processing unit.

In the example shown in FIG. 1, the signal processing system forms part of an ultrasound system, wherein the probe 130, housing the first ASIC 110, further includes an acoustic transducer array 140 adapted to transmit ultrasonic signals and receive echo signals from a subject. Within the first ASIC are a plurality of asynchronous sigma-delta modulators 150, each connected to an associated transducer element 160 of the acoustic transducer array.

Figure 2:
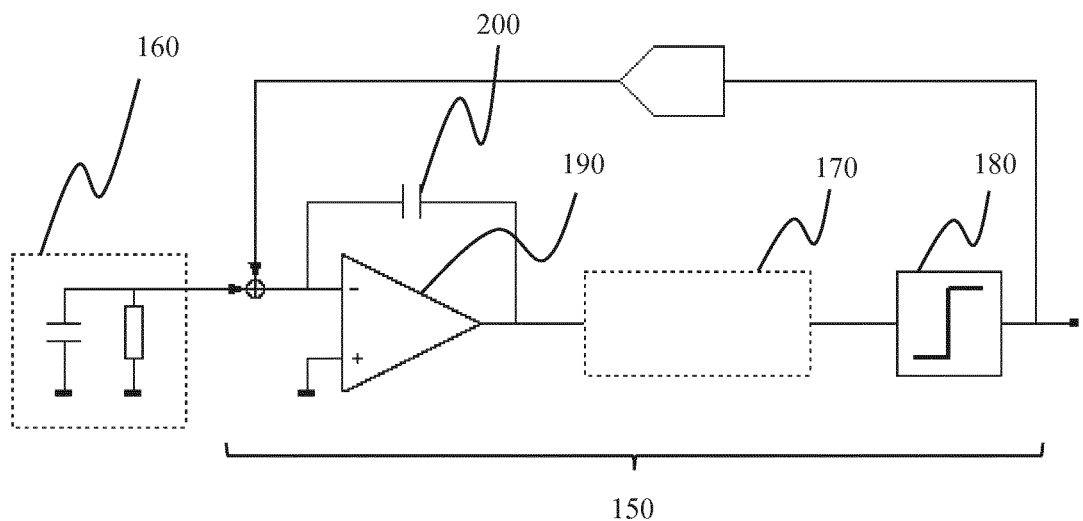
FIG. 2 shows a schematic of an asynchronous sigma-delta modulator.

FIG. 2 shows an asynchronous sigma-delta modulator 150 in more detail connected in series with a transducer element 160. In this example, there is provided an asynchronous sigma-delta modulator for each transducer element, or readout channel, of the probe 130.

Asynchronous sigma-delta modulators are closed-loop non-linear systems that can sustain inherent stable oscillations, denoted as limit cycles, which transform the information in the amplitude of their input signal into time information in their output signal. The limit cycle oscillations are due to a self-oscillation mechanism which is governed by the components of the closed loop asynchronous sigma-delta modulators, such as loop filters 170 and a binary quantizer 180. For an ultrasound system, the input signals typically have a frequency in the range of 2.5-5 MHz. In this case, the self-oscillations of the asynchronous sigma-delta loop will have a frequency of 50 MHz, which is then modulated by the input signal.

The amplitude to time conversion performed by the asynchronous sigma-delta modulator 150 is free of quantization noise and, due to the noise shaping properties of the loop, can be realized with very high accuracy. The achievable performance in a given low-frequency band is determined by the self-oscillation frequency of the asynchronous sigma-delta modulator and the thermal noise of the implementation. The binary time domain signal generated by the asynchronous sigma-delta modulator is fed to the second ASIC 120 for further processing. In the second ASIC the amplitude information can be decoded with a simple low-pass filtering or additional further processing may be performed on the binary time domain signal. The asynchronous sigma-delta modulator, in the absence of an input signal, creates a sequence of positive and negative pulses with a 50% duty cycle at a frequency called the limit cycle idle frequency, or center frequency, that is controlled by construction of the closed loop.

In other words, the asynchronous sigma-delta modulator 150 encodes amplitude information in the time domain in a binary bit-stream. In this way, the signal propagation becomes binary (digital), meaning the signal may be propagated between the first 110 and second 120 ASICs with much higher robustness to interference and cross-talk and at a lower cost to the subsequent processing elements.

The first ASIC 110 may operate at 1.8V, 2.5V or 3.3V according to the application and the second ASIC 120 may operate at voltages from 1.8V down to 1.1V or lower. In the example of an ultrasound system, the transducer array may operate at voltages up to 75V.

In the example shown in FIG. 2, the asynchronous sigma-delta modulator is constructed in a specific way using components customized for signal acquisition from ultrasound transducers. In particular, a input low-noise amplifier 190 (LNA) is incorporated in the asynchronous sigma-delta modulator loop.

The LNA 190 can be configured as either a charge or current integrator by way of a feedback capacitor 200. The feedback signal of this capacitor can be added at the LNA input in current, or charge, depending on the virtual ground provided at that input node. The additional loop stages are required for controlling the phase shift in the asynchronous sigma-delta modulator loop so as to ensure the self-oscillations are achieved at a frequency that exceed at least 10 times the Nyquist frequency of the input signal band. This high oscillation frequency is needed to prevent spurious components from entering the signal band when receiving high amplitude input signals. The loop filters 170 may also be implemented in a passive way, for example using resistors and capacitors.

The loop ends with an asynchronous binary quantizer 180 that creates the binary output signal. The quantizer can directly drive an inverter, which in turn can drive a link to another processing step, such as the second ASIC, for example via a digital buffer.

The operation of asynchronous sigma-delta modulators is discussed further in Ouzounov, S. et al (2006), Analysis and Design of High-Performance Asynchronous Sigma-Delta Modulators With a Binary Quantizer, *IEEE Journal of Solid-State Circuits*, 41(3), pp. 588-596.

Figure 3:
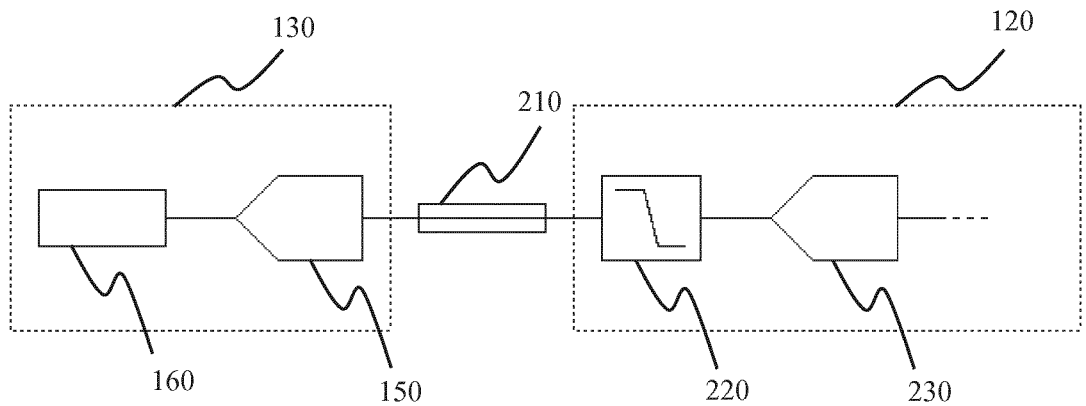
FIG. 3 shows a processing chain of the signal processing system of FIG. 1.

In FIG. 3, the processing chain for one transducer element 160 is shown, wherein an acoustic ultrasound signal is received by the transducer element and propagated to the asynchronous sigma-delta modulator 150, which transforms the acoustic ultrasound signal into a binary time domain signal. This binary bit-stream is then propagated by way of a data channel 210 to the second ASIC, which may, for example, comprise a demodulator 220 and an analog-to-digital converter 230. In the typical case of ultrasound imaging probes the data channel may be a PCB trace connecting the two ASICs. In the case where the signal processing system is implemented into an ultrasonic catheter, the first ASIC is at the tip of the catheter. Then, the data channel may be a galvanic, or an optical, link of a few hundreds of centimeters and the second ASIC may be located at a separate back end processing unit or in the probe handle.

The example shown in FIG. 3 shows the case where one asynchronous sigma-delta modulator 150 is provided for each transducer element 160. Alternatively, several transducer elements may be time multiplexed to one asynchronous sigma-delta modulator or, in another case, the data from several transducer elements may be combined, for example using analog beamforming, before or after each asynchronous sigma-delta modulator.

The implementation of an asynchronous sigma-delta modulator has been described within the context of an ultrasound system; however, this approach may be applied in any situation where it is beneficial to separate the sensor (such as the transducer array) and the post-processing circuitry, which may be due to technology, size or cost limitations. An example of the latter is a DNA sequencing system, where the sensor array is disposable and is produced using an inexpensive and outdated technology. The signal processing, on the other hand, is complex and consumes large amounts of power, so is best implemented in a more advanced technology node. A further example is a sensor on a flexible substrate, for example a foil, which does not support high quality or small feature size devices, required to perform the signal processing.

In a further example, there is provided an asynchronous sigma-delta modulator comprising a time gain function circuit adapted to alter a time gain function of the asynchronous sigma-delta modulator. The time gain function is adapted to control a feedback gain of the asynchronous sigma-delta modulator, thereby controlling a dynamic range of the asynchronous sigma-delta modulator.

Figure 4:
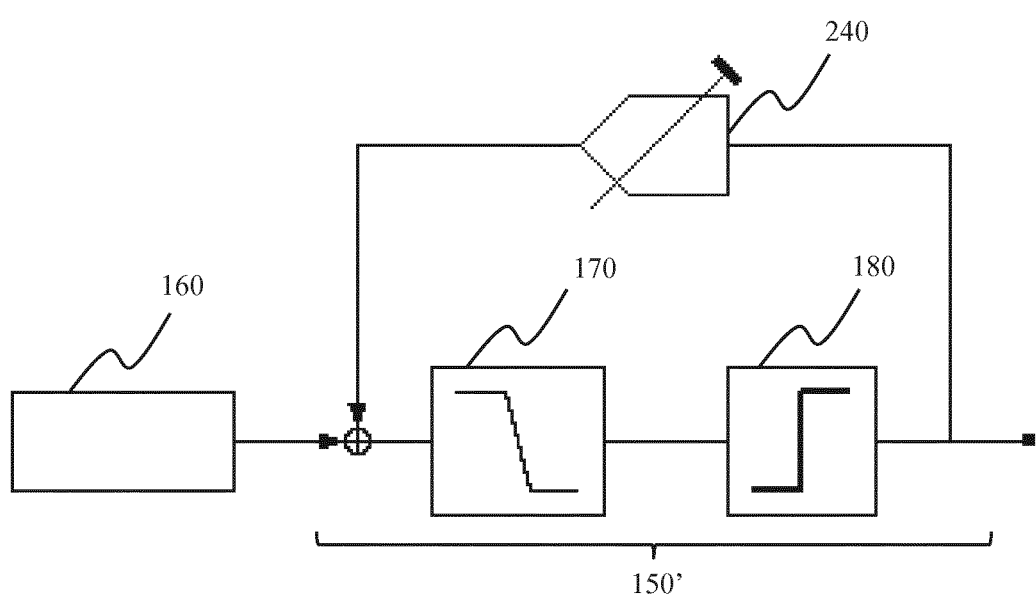
FIG. 4 shows a schematic of an embodiment of the asynchronous sigma-delta modulator comprising a time gain function circuit.

FIG. 4 shows an embodiment of the asynchronous sigma-delta modulator 150' wherein further power optimization can be realized by adding additional functions in the asynchronous sigma-delta modulator loop. This embodiment elaborates the addition of a time gain control (TGC) function by way of a TGC circuit 240. Typically, the asynchronous sigma-delta modulator can be designed to have a large dynamic range for receiving input signals; however, it may not cover the entire dynamic range required by an ultrasound system. The dynamic range may be controlled by TGC functions.

The time gain function may be used to compensate for the received echo signal attenuation as a function of imaging depth. The attenuation of the received echo signals increases with increasing imaging depths and increasing transmit frequencies. The imaging depth of the signal is related to reflection time, meaning that as time progresses, the signal will be increasingly attenuated. The signal attenuation can cause severe signal loss if not compensated.

In general, TGC functions require additional gain stages, such as frequency dependent slide potentiometers that allow the gain to be determined interactively by the user, which in turn occupy chip area and consume large amounts of power. The control of the TGC gain stages is slow and often is performed at a back-end processing unit. Local control loops that detect signal strength and adapt the gain accordingly are too complex to realize accurately and will cause excessive power consumption. The simplest example of a time gain function is a linear increase with time, wherein a steeper linear function may be used where attenuation is higher, for example when high frequency transmit signals are used. Further, a TGC function may be adapted to accommodate knowledge from the user about what is being imaged. In this way, the TGC function enables further optimization of the image quality.

As discussed above, the asynchronous sigma-delta modulator 150', as a principle of operation, encodes analog amplitude information in a binary time domain signal. The encoding is completely asynchronous, meaning there is no need for a local time reference. The dynamic range asynchronous sigma-delta modulator loop is typically scaled to a maximum expected amplitude of the input signal received at the transducer element 160 by dimensioning the feedback signal.

In order to avoid overload, the feedback signal strength is designed to be roughly 25% stronger that the strongest input signal that is expected to appear at the asynchronous sigma-delta modulator 150' input. In ultrasound, and other types of sensory signal acquisition, the input signal is expected to change in time with some known function. For example, in the case of ultrasound, the longer the acquisition time window, the lower the amplitude of the arriving signal due to the deeper reflections of the signals within the body. The asynchronous sigma-delta modulator can be adjusted to accommodate expected changes in the input signal amplitude ranges by adapting the strength of the feedback signal by way of the TGC circuit 240.

The implementation of the TGC function is based on the realization that the first operation of an asynchronous sigma-delta modulator loop is to subtract the feedback signal from the input signal. It should be noted that the feedback signal is time encoded representation of the input signal generated by the asynchronous sigma-delta modulator.

For zero input, the averaged feedback signal is also zero. With an increase in the input signal amplitude, the average feedback signal similarly increases. The point at which the feedback signal cannot match the input signal strength is referred to as the overload point. The dynamic range of the asynchronous sigma-delta modulator lies between zero input and the overload point.

It should be noted that in a practical implementation there is always some noise present in the system due to the building blocks of the asynchronous sigma-delta modulator. The noise level determines the sensitivity of the asynchronous sigma-delta modulator, in other words, the smallest signal amplitude that the asynchronous sigma-delta modulator can encode, and so appear in the asynchronous sigma-delta modulator feedback signal. In order to detect very small signals, which in the context of ultrasound may mean signals from a larger depth and/or with a higher frequency, the noise of the asynchronous sigma-delta modulator should be minimized.

The operation of the TGC circuit may be described according to various imaging depths.

For imaging at close depths, no additional gain is required. The asynchronous sigma-delta modulator feedback is adapted to handle the maximum signal coming from the transducers under these conditions without overload. This means that a maximum feedback signal is used. It should be noted, the minimum input signal that can be encoded, taking inot account noise, also depends on the ratio between input signal strength and feedback strength. When the feedback is too strong, for example 1000 times stronger, the time required to accurately encode these inputs is too high, meaning smaller amplitude signals become "invisible" to the asynchronous sigma-delta modulator.

When the imaging depth is increased, meaning that a longer time has passed since the start of the reception and the desired signals have become weaker. In a classic TGC circuit, extra gain is switched on to compensate for this. In the asynchronous sigma-delta modulator case, this means that the feedback signal can be weakened, for example by scaling it. This means that the asynchronous sigma-delta modulator can detect smaller amplitude signals at the input, thereby resulting in an overall extension of the dynamic range of the asynchronous sigma-delta modulator. The scaling of the feedback can be done multiple times and in a discrete or continuous manner to account for greater imaging depths.

Figure 5:
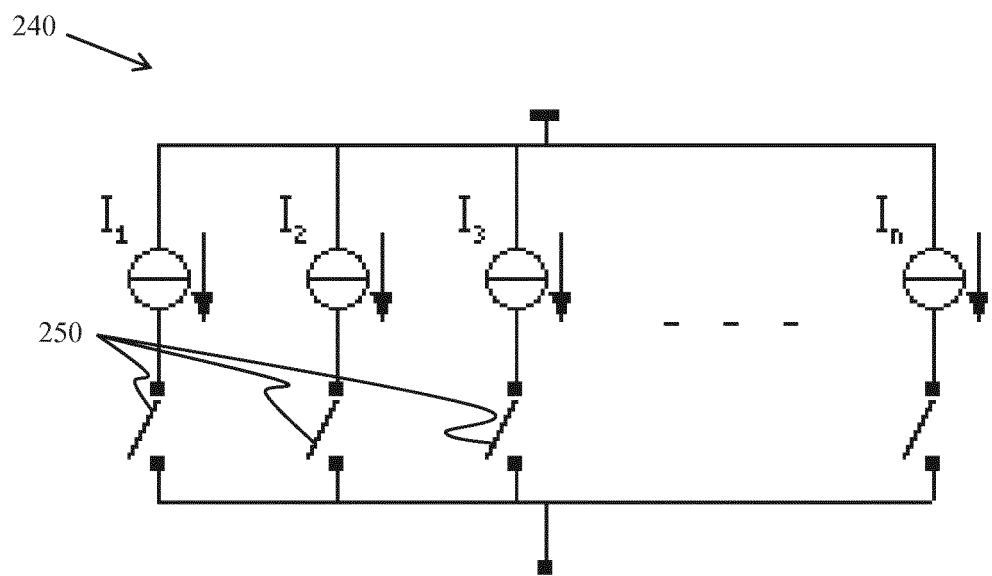
FIG. 5 shows an embodiment of the time gain function circuit shown in FIG. 4.

FIG. 5 shows an example of a possible programmable feedback implementation of the TGC circuit 240. In this case, the TGC circuit includes a set of current sources ($I_1$, $I_2$, ..., $I_N$), each having a different strength, that are selected by a user of the system or by an automatic loop using a set of switches 250. Alternatively, a switched capacitor network may be used in the realization of the TGC circuit where the feedback of capacitors controls the dynamic range scaling of the asynchronous sigma-delta modulator. The charge and discharge of the capacitors is controlled by the binary output signal of the asynchronous sigma-delta modulator. In addition, the TGC circuit is capable of controlling characteristics that determine when and by how much the dynamic range of the asynchronous sigma-delta modulator will be adapted. For example, in the ultrasound machine this can be selected by the user. However, it is often practical to adapt the dynamic range automatically in order to avoid the accidental overload of the asynchronous sigma-delta modulator.

In the context of an asynchronous sigma-delta modulator, the digital-to-analog converter is typically a binary one meaning that when the output of the asynchronous sigma-delta modulator is 1, the digital-to-analog converter produces a positive analog current. When the output of the asynchronous sigma-delta modulator is zero, the digital-to-analog converter produces a negative analog current. The value of the generated current (or the integrated charge in the case of a switched capacitor array) determines the amount of feedback and so the dynamic range of the asynchronous sigma-delta modulator. The minimum possible feedback current should be at least 25% larger than the maximum expected current from the ultrasound transducers when the signals are acquired at a maximum depth. A similar rule applies when low depth imaging is performed where the input signals have a high amplitude. The asynchronous sigma-delta modulator feedback signal amplitude must exceed the maximum expected input signal amplitude by at least 25%.

The binary time domain output signal of the asynchronous sigma-delta modulator is converted to an analog signal, typically current, that is fed back and subtracted from the input signal. When the feedback signal is current, the feedback implementation may for example take the form of a transistor operating as a current source and controlled in an on/off mode by the binary output. There are two feedback parameters: the first being the value of the current, representing the feedback strength and the encoding capability; and the second being how much time the current is on for to encode the input signal. The feedback is adapted by scaling the values of this current source, or by selecting the desired value from a bank of current sources, such as the switched current array. Alternatively, the feedback can be implemented by a resistor acting as a current source.

Figure 6:
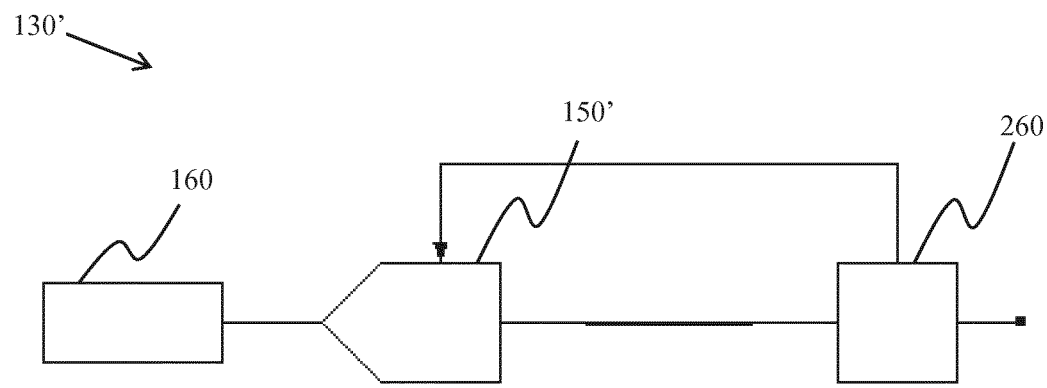
FIG. 6 shows an embodiment of the probe shown in FIG. 1.

FIG. 6 shows an embodiment of the probe 130' shown in FIG. 1, which includes an asynchronous sigma-delta modulator 150' as shown in FIG. 4 and a digital amplitude detector 260 used to estimate the signal amplitude at the input of the asynchronous sigma-delta modulator. The detector may be implemented by a simple counter that reports when more 1s or 0s are counted from the binary bit-stream, generated by the asynchronous sigma-delta modulator, which is a direct measure of the input signal strength. This may then be communicated to the asynchronous sigma-delta modulator, and more specifically to the TGC circuit, in order to alter the TGC function of the asynchronous sigma-delta modulator loop, thereby controlling the dynamic range of the input. As the feedback signal within the asynchronous sigma-delta modulator loop is subtracted from the input, and the error from said subtraction is minimized in time by the loop operations, a stronger feedback signal means that a higher amplitude input signal can be processed by the loop. Similarly, if the processing of lower amplitude signals is desired, the strength of the feedback signal needs to be decreased. In other words, the dynamic range of the asynchronous sigma-delta modulator loop is automatically scaled to fit the input signal.

In a further example, there is provided a method for multiplexing a plurality of analog signals each from a separate channel. The method includes obtaining the plurality of analog signals and generating, in an asynchronous manner, a plurality of quantized time domain signals based on the plurality of analog signals. Finally, the plurality of quantized time domain signals are multiplexed, thereby generating a multiplexed signal in which edge timing events are associated with channel identifiers.

Looking back to FIG. 1, it can be seen that large arrays of transducers may be required in various imaging and sensing applications. Typically, these generate large volumes of data that undergo complex signal processing before the final result is available. Sometimes, the signal processing requires bulky and power-hungry equipment, while the sensing array needs to retain a small size, particularly where freedom of movement of the probe is required. The two processing systems, in the example shown in FIG. 1 these are the first 110 and second 120 ASICS, are then mechanically separated and remain electrically connected by a cable. Normally, the cable contains a separate lead for each transducer element 160 of the transducer array 140. Cables of up to about 260 leads are known to have been used in the industry for such purposes. Each transducer element of the array generates an analog signal that may be converted to a particular (electrical) quantity by the conditioning electronics. Often, no such conversion takes place and the analog signal is simply amplified before being propagated to a remote processing device. The disadvantage of having a dedicated electrical connection between each transducer element 160 of a sensor array 140 and the remote signal processing back-end, on the second ASIC 120, is that it does not scale well for large array sizes. Cables with several hundreds, or even thousands of leads can be manufactured, but are too unwieldy and expensive. Methods exist to combine the signals from a number of elements and transmit them through a single channel, resulting in a reduction of the number of cable leads. However, multiplexing analog signals is generally a complex, power intensive and unreliable process.

Figure 7:
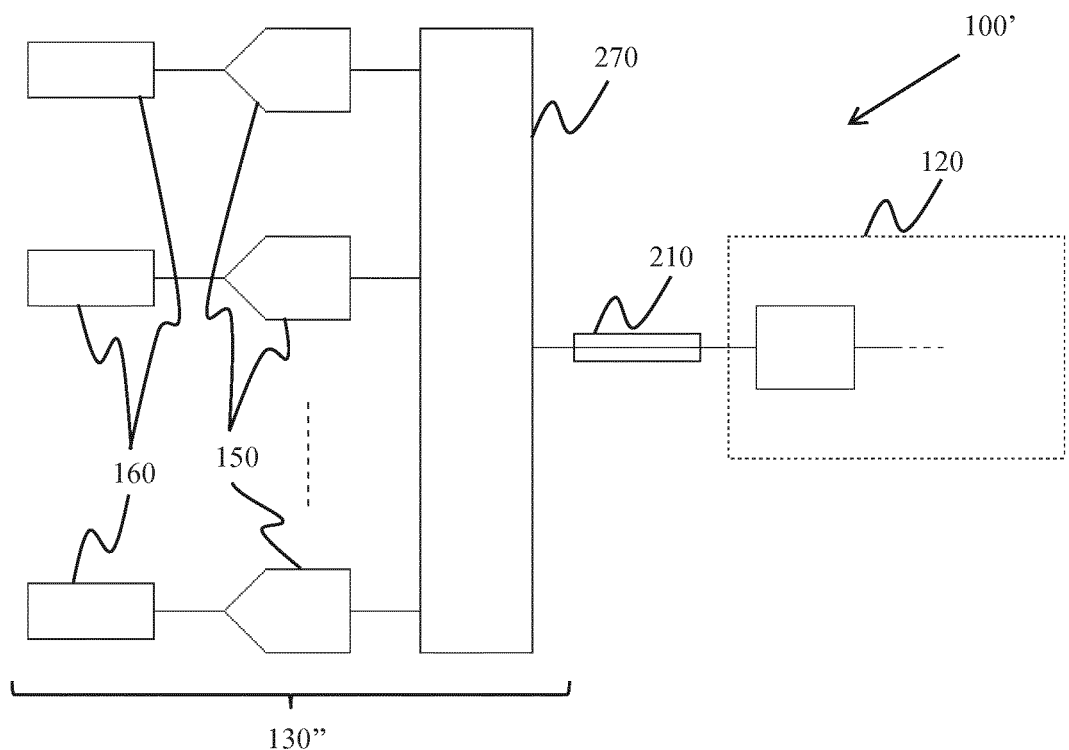
FIG. 7 shows an embodiment of the signal processing system of FIG. 1 comprising a multiplexer.

FIG. 7 shows an embodiment of the signal processing system 100' of FIG. 1, which includes a multiplexer 270 connected to a plurality of asynchronous sigma-delta modulators 150 housed on the first ASIC within the probe 130″. In this case, the analog signals received by the transducer elements are passed through asynchronous sigma-delta modulators, thereby generating a plurality of binary bit-streams in the time domain, which may then be combined into a multiplexed signal. In this way, the cable lead count may be reduced and allow for larger array sizes. In addition, this may be implemented without using a sampling clock in the first ASIC 110, thereby reducing the number of components and power consumption required to propagate the signals between the first 110 and second 120 ASIC.

In other words, the asynchronous sigma-delta modulators 150 convert the acoustic signal from each transducer element 160 to the time domain. A multiplexer 270 then encodes each event from the transducer array and transmits it through a data channel 210 to a second ASIC 120. The exact number of conductors within the data channel depends on the implementation of the multiplexer. If a fully serial communication is chosen, in principle, the transmission may be achieved using a single transmission lead and a reference lead. The remote processing unit comprises a second ASIC 120 adapted to interpret the multiplexed signal. In some examples the ASIC comprises a time to digital converter, the function of which is described further below. Using the measurements from the second ASIC, the binary bit-stream can be reconstructed entirely in the digital domain.

Figure 8:
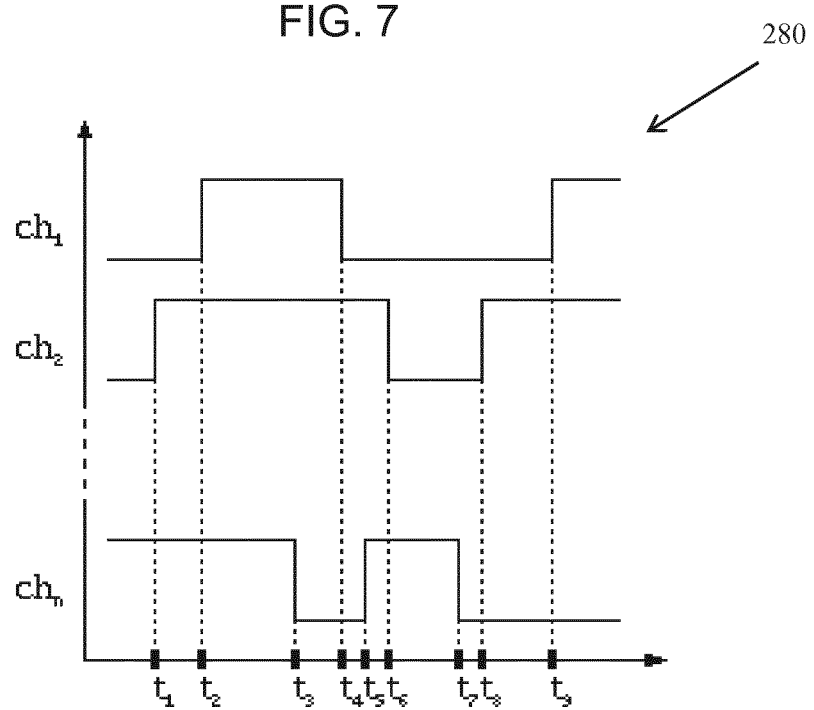
FIG. 8 shows a plot of several exemplary signals generated by an asynchronous sigma-delta modulator.

FIG. 8 shows a plot 280 of several exemplary binary bit-streams, each from an asynchronous sigma-delta modulator 150 of the probe 130″, arranged according to which channel (transducer element 160) the signal was originally received at. Signals are shown for three channels in this example ($ch_1$, $ch_2$ and $ch_N$), where N is the total number of channels and will vary according to the application in question. The rising and falling edges of each binary bit-stream waveform are not synchronous and may occur at an arbitrary moment.

As the timing of the edge timing events of each waveform is significant, the multiplexer 270 may treat each rising or falling edge as a separate edge timing event. For example, the multiplexer may label each edge timing event with a unique (digital) identifier and convey them to the second ASIC in an asynchronous fashion.

For example, as shown in FIG. 8: at time $t_1$ the multiplexer signals a rising edge of channel 2; at time $t_2$ the multiplexer signals a rising edge of channel 1; at time $t_3$ the multiplexer signals a falling edge of channel 3; and so on.

The signaling scheme shown in FIG. 8 may be implemented, for example, by transmitting a number corresponding to the channel number, in combination with a number representing the edge type of the edge timing event (i.e., rising or falling) at the appropriate moment in time in the multiplexed signal. In the example shown in FIG. 8, at time instant:

$t_1$: the number 2, corresponding to channel 2, together with the number 1, corresponding to a rising edge is sent, $t_2$: the number 1, corresponding to channel 1, together with the number 1, corresponding to a rising edge is sent, $t_3$: the number 3, corresponding to channel 3, together with the number 0, representing a falling edge is sent.

Depending on the architecture of the multiplexer and the link to the second ASIC, these combinations of numbers may be sent either in a parallel or a serial fashion. For example, should the total number of channels be three and a parallel binary signaling be chosen, at $t_1$ the transmitted binary word could be 101 (i.e., channel number, followed by edge type identifier), at $t_2$ 011, and at $t_3$ 110. Any other appropriate implementation may be chosen according to the application. The receiving end at the second ASIC is event-driven and will react to each change of the input signal. As the occurrence of two consecutive codes of the same value (i.e., two consecutive rising or falling edges on the same channel) is precluded, there would be no missed edge timing events.

Since the time of transmission of each edge timing event identifier by the multiplexer 270 coincides with the occurrence of the event it describes, it is possible to reconstruct the entire data stream at the second ASIC 120 by timestamping each incoming event identifier, or by measuring the time between received events. It is possible that two or more edge timing events may occur at the same time, particularly for systems with lower time resolutions. Concurrent edge timing events may be detected concurrently, but processed sequentially. The timing error this will result in will appear as random error in the signal arriving at the second ASIC and will be filtered out by the noise shaping function. In other words, concurrent events can be buffered and transmitted sequentially, with a minimum penalty to accuracy.

In a further example, there is provided a system for performing analog-to-digital conversion, the system comprising: a probe having a first ASIC; a processing unit having a second ASIC; and a data channel. The first ASIC is adapted to receive an analog signal and output a binary bit-stream comprising asynchronous time-domain pulses. The second ASIC is adapted to receive the binary bit-stream; and generate a digital output based on time-to-digital conversion. The data channel is adapted to propagate the binary bit-stream from the first ASIC to the second ASIC, wherein the first and second ASICs are spatially separated.

Figure 9:
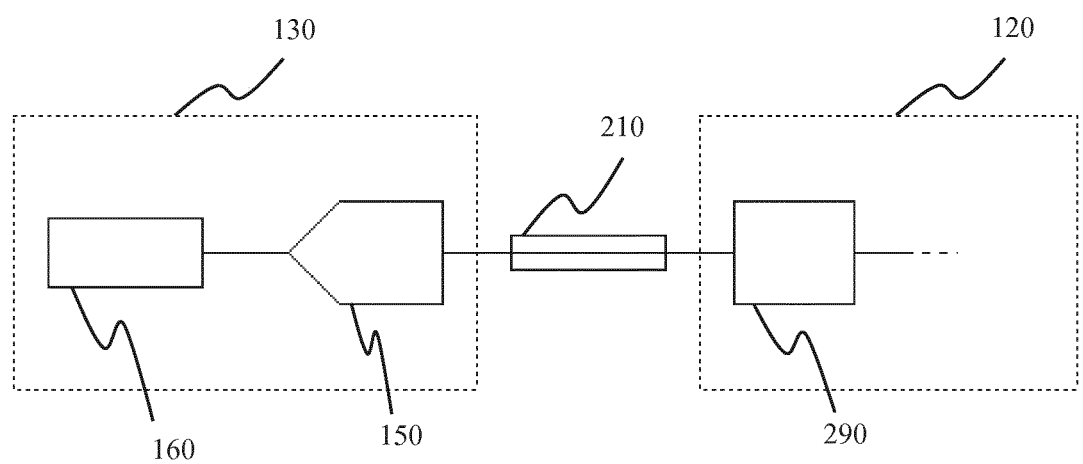
FIG. 9 shows an embodiment of the signal processing system of FIG. 1 comprising a time-to-digital converter.

FIG. 9 shows an embodiment of the processing chain shown in FIG. 3, wherein the probe 130 comprises a transducer element 160 and an asynchronous sigma-delta modulator 150. In addition, the second ASIC 120, connected to the first ASIC within the probe by way of the data channel 210, comprises a time-to-digital converter 290. In other words, the signal processing system comprises a spatially distributed asynchronous sigma-delta modulator and time-to-digital converter across two different technologies, the first 110 and second 120 ASICS, and, in some applications, at a large distance from each other depending on the specific needs of the ultrasound system.

As discussed above, the asynchronous sigma-delta modulator encodes the incoming analog amplitude information in a binary time domain signal and the encoding is completely asynchronous. Thus, the time-to-digital converter 290 may act to retrieve the encoded amplitude information from the binary bit-stream generated by the asynchronous sigma-delta modulator 150. Following the time-to-digital conversion, the retrieved data, now in a digital form, may be used to analyze the original analog signals. In the case that the signal processing system is included within an ultrasound system, the retrieved data may be used to construct an ultrasound image.

As the data leaving the asynchronous sigma-delta modulator 150 is asynchronous, the time-to-digital converter 290 operates using an internal clock signal so as to correctly order and correlate the incoming signals.

The clock frequency of the time-to-digital converter, in the current embodiment, is a function of the required dead time. The dead time depends on the maximum acceptable error during signal reconstruction, while still being able to achieve the required SNR.

The time-to-digital converter may be configured to operate in a number of ways, such as measuring the time between events or simply timestamping events as they arrive; however, in the case of interpreting the asynchronous signals generated by the asynchronous sigma-delta modulator, the preferred mode of operation is to measure the length of time between two events in the time domain. As such, it will be unable to timestamp these events, unless additional circuitry is present that accumulates the time differences and represents them as a total time elapsed from an arbitrary starting point. Of course, timestamping could be used instead of measuring the time between successive events, but a sufficiently accurate time reference would be needed, which would most likely be less power-efficient.

In a system where each transducer element 160 is connected to an individual asynchronous sigma-delta modulator 150, which is connected to an individual time-to-digital converter 290, the first mode of operation may be preferred. Alternatively, in the case where multiple transducer elements are connected to a single asynchronous sigma-delta modulator, the time-to-digital converter may be operated in the second mode. In a further example, in the case where the signals of multiple asynchronous sigma-delta modulators are multiplexed and received by a single time-to-digital converter, as described above, the time-to-digital converter may be operated in the second mode.

In a further example, there is provided a pipeline time-to-digital converter comprising a coarse time-to-digital converter and a fine time-to-digital converter block. The coarse time-to-digital converter is adapted to: receive an incoming signal and output both: a coarse digital output; and a coarse residue time. The fine time-to-digital converter block receives the coarse residue time and comprises one or more fine time-to-digital converters connected in series. Each of the one or more fine time-to-digital converters is adapted to receive an incoming residue time from the previous fine, or coarse, time-to-digital converter in the series and output both: an outgoing residue time to the subsequent fine time-to-digital converter in the series; and a fine digital output.

Figure 10:
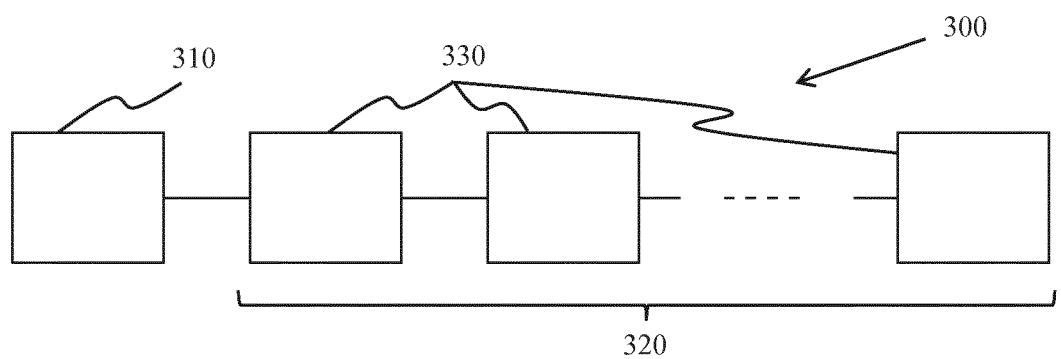
FIG. 10 shows a schematic of a pipelined time-to-digital converter.

FIG. 10 shows a schematic representation of a pipelined time-to-digital converter 300. The pipelined time-to-digital converter includes a coarse time-to-digital converter 310 and a fine time-to-digital converter block 320, which comprises a plurality of fine time-to-digital converters 330.

Typically, a time-to-digital converter is needed to handle information in the time domain, such as the binary bitstream generated by an asynchronous sigma-delta modulator as described above. In this case, the information signal at the input of the TDC consists of a sequence of events, represented by pulses. The time-to-digital converter may measure the time between two pulses, and represent it as a digital signal. The time between these pulses has to be determined with sufficient fidelity for correct signal processing to Occur.

Several performance characteristics of the time-to-digital converter are central to achieving such fidelity. Firstly, each time period must be measured with sufficient accuracy and, the converter must be able to commence subsequent measurements sufficiently quickly after a preceding one. The time between the end of a measurement and the commencement of a new one is referred to as the dead time. In an idealized scenario, the dead time of a time-to-digital converter is zero. Finally, the converter must be able to detect the whole range of time periods generated by the first ASIC 110, and more specifically the asynchronous sigma-delta modulator 150. In other words, the time-to-digital converter must have a sufficient dynamic range.

Typically, there is a trade-off between resolution and dead time in conventional time-to-digital converter designs. Increasing the resolution of a converter normally leads to an increase in the dead time. Of course, it is possible to optimize both parameters, but at the expense of power consumption. For example, a continuously running high frequency converter will have a resolution proportional to the bit aperture and a dead time inversely proportional to the frequency of operation. However, the power dissipation will be proportional to both parameters, meaning such designs are rarely feasible.

The pipelined time-to-digital converter 300 shown in FIG. 10 achieves both a high resolution and a low dead time, without compromising on power dissipation. The pipelined time-to-digital converter is comprised of a number of cascaded individual time-to-digital converter stages. The first stage is a low latency, coarse time-to-digital converter 310, for example based on a ring oscillator or counter, which runs at a low frequency for low power consumption. The frequency of the ring oscillator is inversely proportional to the dead time of the time-to-digital converter.

Each measurement by the coarse time-to-digital converter 310 generates an error, referred to as the residue time, which needs to be determined and accounted for in order to obtain a high resolution. The residue is measured in a following stage that that consists of a fine time-to-digital converter 330. The residue of this second stage is then fed to another fine time-to-digital converter and this is repeated until the desired resolution is reached.

Figure 11:
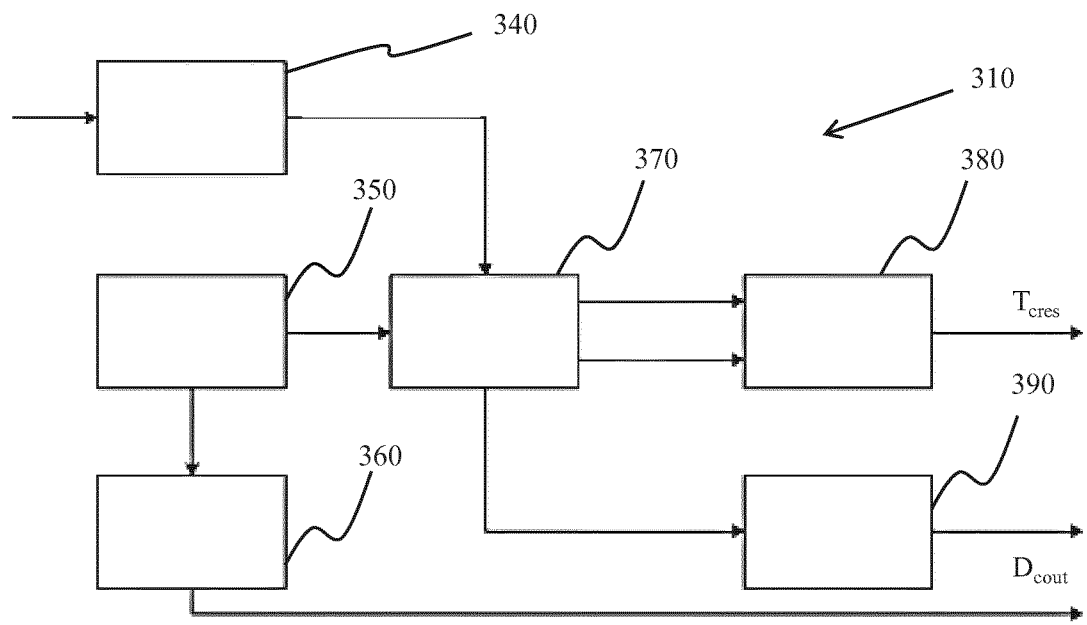
FIG. 11 shows a schematic of a coarse time-to-digital converter.

FIG. 11 shows the coarse time-to-digital converter 310 in more detail.

In the embodiment shown in FIG. 11, the incoming signals are first received by a multiplexer 340, which may be adapted to combine incoming signals from multiple channels into a single signal to be passed through the coarse time-to-digital converter. The pulses generated by the multiplexer may act as a trigger signal for the time-to-digital converter. In the case where the time-to-digital converter is only receiving signals from a single source, for example in the case where the multiplexer is included on the first ASIC 110 as described above, the multiplexer 340 may be excluded.

In order to measure the arrival time of the incoming signal, referred to as the trigger pulse, and produce a residue time, the time-to-digital must both: store the state of a ring oscillator 350 when the trigger pulse arrives; and combine the output of the ring oscillator following the trigger pulse with the initial trigger pulse itself. The second operation produces the residue time of the coarse time-to-digital converter. In addition, the ring oscillator is coupled to a counter 360, which acts to increase the dynamic range of the coarse time-to-digital converter.

The signal from the ring oscillator and the trigger pulse from the multiplexer are both passed to a selector 370, the core component of which is a D flip-flop. The signal from the ring oscillator acts as a clock signal for the D flip-flop and the trigger pulse form the multiplexer acts as the clear (CLR) signal. The D gate of the D flip-flop is held at a high level. The output of the D flip-flop, and so the output of the selector, will only rise to a high level when both the ring oscillator signal and the trigger pulse are high. In this way, only trigger pulses following a ring oscillator pulse will be passed by the selector.

The output of the selector 370 is then passed to a time amplifier 380, which generates a coarse residue time, $T_{cres}$, and to an encoder 390, which generates a coarse digital output, $D_{cout}$. In this case, the time amplifier is a D flip-flop pulse train amplifier and the encoder is a binary encoder. The coarse residue time, $T_{cres}$, is then passed to the fine time-to-digital converter block 320.

Figure 12:
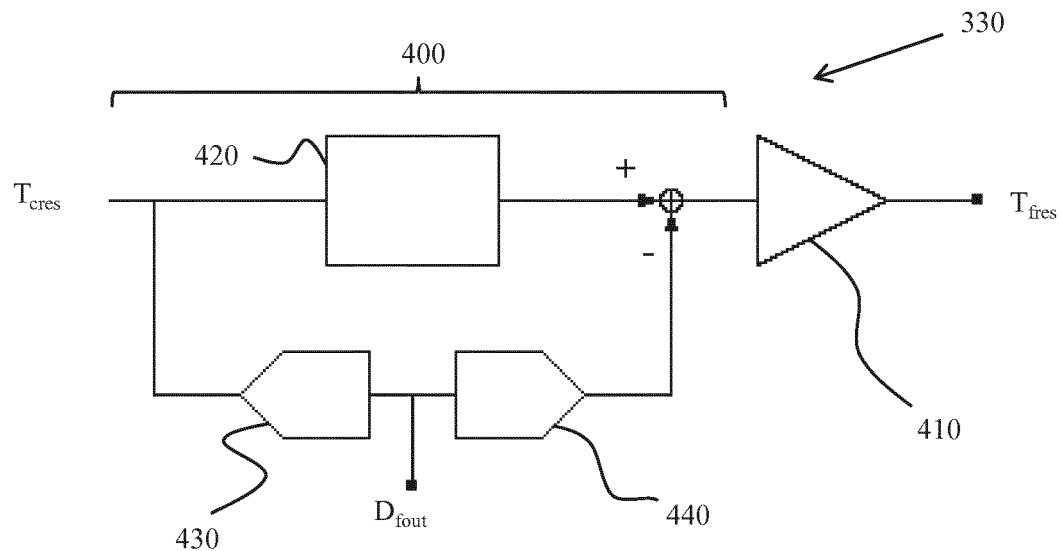
FIG. 12 shows a schematic of a fine time-to-digital converter.

FIG. 12 shows a fine time-to-digital converter 330 in more detail.

Each of the fine time-to-digital converter 330 stages of the fine time-to-digital converter block 320 are identical and comprise a low bandwidth converter 400 followed by a time amplifier 410. The low bandwidth converter comprises a time register 420 and a conventional time-to-digital converter 430, both adapted to receive the coarse residue time, $T_{cres}$. The conventional time-to-digital converter generates a fine digital output, $D_{fout}$, which may then be output from the fine time-to-digital converter and be combined with the coarse digital output, $D_{cout}$, to generate a final digital output of the pipelined time-to-digital converter.

The fine digital output, $D_{fout}$, is then passed through a digital-to-time converter 440 and subtracted from the coarse time residue, $T_{cres}$, measured by the time register. As the conversions are not exact, this subtraction will result in a small residue time. This is then passed through the time amplifier 410 to amplify the residue of the converter, so that it matches the dynamic range of the following stage, thereby generating a fine residue time, $T_{fres}$. The time amplifier block amplifies the error signal of the respective stage in the pipeline in order to enable high resolution comparison at the subsequent stages.

It should be noted that the maximum time period that should be detectable by the low bandwidth converter is the inverse of the operating frequency of the first stage, and more specifically, the inverse of the ring oscillator.

The residue time may be passed through any number of fine time-to-digital converter 330 stages according to the resolution of the final digital output required by the given application.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A signal processing system, for transferring analog signals from a probe to a remote processing unit, comprising:
a first ASIC at the probe, adapted to receive an analog probe signal acquired from a subject, wherein the first ASIC comprises:
an asynchronous sigma-delta modulator, wherein the asynchronous sigma-delta modulator is adapted to:
receive the analog probe signal; and
output a binary bit-stream comprising asynchronous time-domain pulses;
a second ASIC at the remote processing unit, adapted to receive the binary bit-stream, and wherein:
the asynchronous sigma-delta modulator comprises:
a time gain function circuit adapted to alter a time gain function of the asynchronous sigma-delta modulator over time, wherein the time gain function is adapted to:
control a feedback gain of the asynchronous sigma-delta modulator, thereby controlling a dynamic range of the asynchronous sigma-delta modulator; and wherein the time gain function circuit is further adapted to alter a time gain function of the asynchronous sigma-delta modulator based on a user imput relating to an imaging depth of the probe.

2. A signal processing system as claimed in claim 1, wherein the signal processing system further comprises a data channel adapted to propagate the binary bit-stream from the first ASIC to the second ASIC.

3. A signal processing system as claimed in claim 1, wherein the first ASIC operates at a voltage greater than or equal to 1.8V, for example 2.5V, and wherein the second ASIC operates a voltage less than or equal to 1.8V, for example 1.1V.

4. A signal processing system as claimed in claim 1, wherein the asynchronous sigma-delta modulator comprises a low noise amplifier.

5. A signal processing system as claimed in claim 4, wherein the asynchronous sigma-delta modulator further comprises a feedback capacitor connected with:
an output of the low noise amplifier; and
an input of the low noise amplifier.

6. A signal processing system as claimed in claim 1, wherein the asynchronous sigma-delta modulator further comprises a low-pass filter.

7. A signal processing system as claimed in claim 1, wherein the asynchronous sigma-delta modulator further comprises an asynchronous binary quantizer.

8. A signal processing system as claimed in claim 1, wherein the asynchronous sigma-delta modulator comprises a feedback digital-to-analog converter.

9. A signal processing system as claimed in claim 1, wherein the first ASIC further comprises an acoustic transducer element, wherein the acoustic transducer element is adapted to receive an incoming acoustic signal and output the acoustic signal.

10. A signal processing system as claimed in claim 1, wherein the second ASIC comprises a demodulator.

11. A signal processing system as claimed in claim 10, wherein:
the demodulator is adapted to:
receive the binary bit stream; and
output a reconstructed analog signal; and
the second ASIC further comprises an analog-to-digital converter adapted to receive the reconstructed analog signal.

12. A signal processing system as claimed in claim 1, wherein:
the probe is an ultrasonic probe; and
the remote processing unit is a back-end signal processing unit.

13. A method for transferring analog signals from a probe to a remote processing unit, the method comprising:
receiving an analog signal from an imaging depth within a subject at a first ASIC at the probe;
performing asynchronous sigma-delta modulation on the analog signal, by way of an asynchronous sigma-delta modulator, thereby generating a binary bit-stream; and
receiving the binary bit-stream from a data channel at a second ASIC at the remote processing unit, and wherein:
performing asynchronous sigma-delta modulation on the analog signal comprises:
altering a time gain function of the asynchronous sigma-delta modulator based on the imaging depth, wherein the time gain function is adapted to:

control a feedback gain of the asynchronous sigma-delta modulator, thereby controlling a dynamic range of the asynchronous sigma-delta modulator.

14. A method as claimed in claim 13, wherein the analog signal comprises an ultrasound signal.

15. A computer program comprising computer program code means which is adapted, when said computer program is run on a computer, to implement the method of claim 13.

* * * * *